United States Patent
Mogensen et al.

(10) Patent No.: US 7,258,680 B2
(45) Date of Patent: Aug. 21, 2007

(54) DEVICE FOR SUBCUTANEOUS ADMINISTRATION OF A MEDICAMENT TO A PATIENT

(75) Inventors: Lasse Wesseltoft Mogensen, Søborg (DK); Magnus Walter Göransson, Göteborg (SE)

(73) Assignee: Unomedical A/S, Birkeroed (DE)

( * ) Notice: Subject to any disclaimer, the term of this patent is extended or adjusted under 35 U.S.C. 154(b) by 0 days.

(21) Appl. No.: 10/517,153

(22) PCT Filed: Sep. 1, 2003

(86) PCT No.: PCT/DK03/00569

§ 371 (c)(1),
(2), (4) Date: Dec. 6, 2004

(87) PCT Pub. No.: WO2004/020038

PCT Pub. Date: Mar. 11, 2004

(65) Prior Publication Data

US 2006/0074380 A1     Apr. 6, 2006

(30) Foreign Application Priority Data

Sep. 2, 2002    (DK) .............................. 2002 01284

(51) Int. Cl.
  *A61M 5/32* (2006.01)
(52) U.S. Cl. .................................... 604/177
(58) Field of Classification Search ............. 604/48, 604/174, 905, 246, 256, 326, 93.01, 546, 604/104, 177; 128/912, DIG. 6, DIG. 26; 24/570, 71.1, 563, 115 H, 546, 127
See application file for complete search history.

(56) References Cited

U.S. PATENT DOCUMENTS

| 643,544 | A | 2/1900 | Simmons |
| 1,838,825 | A | 12/1931 | Goldstein |

(Continued)

FOREIGN PATENT DOCUMENTS

DE        893 296        12/1953

(Continued)

OTHER PUBLICATIONS

International Search Report, dated Jan. 21, 2004.

*Primary Examiner*—Nicholas D. Lucchesi
*Assistant Examiner*—Christopher D. Koharski
(74) *Attorney, Agent, or Firm*—Brinks Hofer Gilson & Lione

(57) ABSTRACT

A device for subcutaneous administration of a medicament to a patient is disclosed, including a cannula housing with an interior chamber, a cannula connected to the housing and being in flow communication with the chamber, a flexible tubing having a first end and a second end, the first end being coupled to the housing such that the tubing is in flow communication with the chamber, and wherein, the second end carries a source coupling for coupling the tubing to the medicament. The tubing between the first and the second end is folded for forming a configuration with at least two essentially parallel courses of tubing, the tubing is secured in the configuration by a first holder device arranged between the first and second end of the tubing; and that the tubing can be displaced in relation to the first holder device for varying the length of the courses of tubing.

27 Claims, 6 Drawing Sheets

U.S. PATENT DOCUMENTS

| | | |
|---|---|---|
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 4,014,328 A | 3/1977 | Cluff et al. |
| 4,146,113 A | 3/1979 | Gavel |
| 4,150,798 A | 4/1979 | Aragon |
| 4,188,950 A | 2/1980 | Wardlaw |
| 4,227,528 A | 10/1980 | Wardlaw |
| 4,267,836 A | 5/1981 | Whitney et al. |
| 4,306,705 A | 12/1981 | Svenson |
| D267,199 S | 12/1982 | Koenig |
| 4,365,630 A | 12/1982 | McFlarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A * | 8/1986 | Wilder et al. ............... 604/180 |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olsen |
| 5,024,662 A | 6/1991 | Menes et al. |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,384,174 A | 1/1995 | Ward et al. |
| 5,387,197 A | 2/1995 | Smith et al. |
| 5,388,931 A | 2/1995 | Carlson |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,487,506 A | 1/1996 | Drummond et al. |
| 5,490,841 A | 2/1996 | Landis |
| 5,492,313 A | 2/1996 | Pan et al. |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A * | 6/1996 | Teissen-Simony .......... 604/177 |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,636 A | 10/1996 | Utterberg |
| 5,584,813 A | 12/1996 | Livingston et al. |
| 5,591,188 A | 1/1997 | Waisman |
| 5,599,309 A | 2/1997 | Marshall et al. |

| | | |
|---|---|---|
| 5,599,315 A | 2/1997 | McPhee |
| 5,599,318 A | 2/1997 | Sweeney et al. |
| 5,643,214 A | 7/1997 | Marshall |
| 5,643,216 A * | 7/1997 | White .......................... 604/174 |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,681,323 A | 10/1997 | Arick |
| 5,695,476 A | 12/1997 | Harris |
| 5,704,920 A | 1/1998 | Gyure |
| 5,709,516 A | 1/1998 | Peterson et al. |
| 5,714,225 A | 2/1998 | Hansen et al. |
| 5,741,288 A | 4/1998 | Rife |
| 5,752,923 A | 5/1998 | Terwilliger |
| 5,810,835 A | 9/1998 | Ryan et al. |
| 5,820,598 A | 10/1998 | Gazza et al. |
| D402,538 S | 12/1998 | Wagter et al. |
| 5,851,197 A | 12/1998 | Marano et al. |
| 5,865,806 A | 2/1999 | Howell |
| 5,873,540 A | 2/1999 | Hardin |
| 5,899,886 A | 5/1999 | Cosme |
| 5,915,640 A | 6/1999 | Wagter et al. |
| 5,916,199 A * | 6/1999 | Miles .......................... 604/174 |
| 5,925,032 A | 7/1999 | Clements |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,968,011 A | 10/1999 | Larsen et al. |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| 5,992,787 A | 11/1999 | Burke |
| 6,017,328 A | 1/2000 | Fischell et al. |
| 6,039,629 A | 3/2000 | Mitchell |
| 6,042,570 A | 3/2000 | Bell et al. |
| 6,045,533 A | 4/2000 | Kriesel et al. |
| 6,050,976 A | 4/2000 | Thorne et al. |
| 6,056,718 A | 5/2000 | Funderburk et al. |
| 6,074,371 A | 6/2000 | Fischell |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A * | 8/2000 | Reekie .......................... 24/518 |
| 6,120,482 A | 9/2000 | Szabo |
| 6,123,690 A | 9/2000 | Mejslov |
| 6,132,755 A | 10/2000 | Eicher et al. |
| 6,183,464 B1 | 2/2001 | Sharp et al. |
| 6,193,694 B1 | 2/2001 | Bell et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,379,335 B1 | 4/2002 | Rigon et al. |
| D456,692 S | 5/2002 | Epstein |
| 6,387,076 B1 | 5/2002 | Van Lunduyt |
| 6,488,663 B1 | 12/2002 | Steg |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,629,949 B1 | 10/2003 | Douglas |
| 6,685,674 B2 | 2/2004 | Douglas et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,749,589 B1 | 6/2004 | Douglas et al. |
| 6,790,199 B1 | 9/2004 | Gianakos |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,880,701 B2 | 4/2005 | Bergeron et al. |
| 6,916,017 B2 | 7/2005 | Noe |
| 6,923,791 B2 | 8/2005 | Douglas |
| 6,926,694 B2 | 8/2005 | Marano-Ford et al. |
| 6,949,084 B2 | 9/2005 | Marggi et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039401 A1 | 11/2001 | Ferguson et al. |
| 2001/0041875 A1 | 11/2001 | Higuchi et al. |
| 2002/0022855 A1 | 2/2002 | Bobroff et al. |
| 2002/0068904 A1 | 6/2002 | Pluth et al. |
| 2002/0072720 A1 | 6/2002 | Hague et al. |
| 2002/0107489 A1 | 8/2002 | Lee |
| 2002/0111581 A1 | 8/2002 | Sasso |
| 2002/0145073 A1 | 10/2002 | Swanson |
| 2002/0156427 A1 | 10/2002 | Suzuki et al. |
| 2002/0161332 A1 | 10/2002 | Ramey |
| 2002/0169419 A1 | 11/2002 | Steg |
| 2002/0173748 A1 | 11/2002 | McConnell et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0069548 A1 | 4/2003 | Connelly et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |

| | | | |
|---|---|---|---|
| 2004/0158207 A1 | 8/2004 | Hunn et al. | |
| 2004/0162518 A1 | 8/2004 | Connelly et al. | |
| 2004/0171989 A1 | 9/2004 | Horner et al. | |
| 2004/0178098 A1 | 9/2004 | Swenson et al. | |
| 2004/0186446 A1 | 9/2004 | Ohshima | |
| 2004/0199123 A1 | 10/2004 | Nielsen | |
| 2004/0204687 A1 | 10/2004 | Mogensen et al. | |
| 2004/0204690 A1 | 10/2004 | Yashiro et al. | |
| 2004/0220528 A1 | 11/2004 | Garcia, Jr. | |
| 2004/0238392 A1 | 12/2004 | Peterson et al. | |
| 2004/0243065 A1 | 12/2004 | McConnell et al. | |
| 2004/0254433 A1 | 12/2004 | Bandis et al. | |
| 2004/0260235 A1 | 12/2004 | Douglas | |
| 2004/0260250 A1 | 12/2004 | Harris et al. | |
| 2005/0035014 A1 | 2/2005 | Cane | |
| 2005/0101932 A1 | 5/2005 | Cote et al. | |
| 2005/0101933 A1 | 5/2005 | Marrs et al. | |
| 2005/0107743 A1 | 5/2005 | Fangrow, Jr. | |
| 2005/0113761 A1 | 5/2005 | Faust et al. | |
| 2005/0119637 A1 | 6/2005 | Lundgren et al. | |
| 2005/0124936 A1 | 6/2005 | Mogensen et al. | |
| 2005/0159709 A1 | 7/2005 | Wilkinson | |
| 2005/0215979 A1 | 9/2005 | Konerup et al. | |
| 2005/0277892 A1 | 12/2005 | Chen | |
| 2005/0283114 A1 | 12/2005 | Bresina et al. | |

FOREIGN PATENT DOCUMENTS

| | | |
|---|---|---|
| DE | 1 053 541 | 3/1959 |
| DE | 26 20 009 A1 | 12/1977 |
| DE | 26 29 009 | 12/1977 |
| DE | 28 03 509 | 8/1979 |
| DE | 28 03 509 A | 8/1979 |
| DE | 37 15 965 A | 1/1988 |
| DE | 196 31 921 | 3/1997 |
| DE | 298 18 311 U1 | 3/1999 |
| DE | 298 18 311 U1 | 11/1999 |
| DE | 19847143 A1 | 1/2000 |
| DE | 101 06 074 A1 | 9/2000 |
| DE | 299 21 406 | 1/2001 |
| DE | 101 06 074 A1 | 6/2002 |
| DE | 299 21 406 U1 | 11/2002 |
| DK | 37 22 893 C1 | 6/1988 |
| DK | 38 23 447 | 2/1996 |
| DK | 196 10 692 A1 | 9/1997 |
| DK | 198 47 143 A1 | 1/2000 |
| DK | 100 49 001 A1 | 4/2002 |
| EP | 0 188 014 B1 | 10/1985 |
| EP | 0 239 244 B1 | 2/1987 |
| EP | 0 298 521 B1 | 9/1990 |
| EP | 0 184 231 B1 | 1/1992 |
| EP | 0 475 857 | 3/1992 |
| EP | 0 544 837 B1 | 6/1993 |
| EP | 0 633 039 | 7/1994 |
| EP | 0 651 662 B1 | 5/1995 |
| EP | 0 714 631 B1 | 6/1996 |
| EP | 744 183 A2 | 11/1996 |
| EP | 0 747 006 A1 | 12/1996 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0 956 879 A1 | 11/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |
| EP | 1 167 765 A2 | 1/2002 |
| EP | 0 775 501 | 6/2002 |
| EP | 0 894 216 B1 | 7/2003 |
| EP | 0 956 879 A1 | 7/2004 |
| FR | 576 849 | 8/1924 |
| FR | 576849 | 8/1924 |
| FR | 2 611 013 | 8/1988 |
| FR | 2725902 | 10/1994 |
| FR | 2 733 915 | 11/1996 |
| FR | 2733915 A1 | 11/1996 |
| FR | 2 781 617 A1 | 1/2000 |
| FR | 2781617 A1 | 1/2000 |
| GB | 478803 | 1/1938 |
| GB | 591730 | 3/1946 |
| GB | 906574 | 9/1962 |
| GB | 1 268 575 | 3/1972 |
| GB | 1 403 034 | 8/1975 |
| GB | 2 224 808 A | 5/1990 |
| GB | 2 270 552 A | 3/1994 |
| JP | 05326062 A | 12/1993 |
| JP | 5326062 A | 12/1993 |
| JP | 7051251 | 11/1995 |
| JP | 9217584 A | 9/1997 |
| JP | 2000-59877 A | 2/2000 |
| JP | 3140740 | 2/2000 |
| JP | 2000059877 A | 2/2000 |
| JP | 3140740 B2 | 3/2001 |
| JP | 2002-028246 | 1/2002 |
| NL | 1017427 C | 11/2002 |
| WO | WO87/06474 | 11/1987 |
| WO | WO93/03787 | 3/1993 |
| WO | WO93/05840 | 4/1993 |
| WO | WO94/20160 | 9/1994 |
| WO | WO95/28327 A | 10/1995 |
| WO | WO96/35472 | 11/1996 |
| WO | WO98/09065 | 3/1998 |
| WO | WO98/58693 | 12/1998 |
| WO | WO99/07435 | 2/1999 |
| WO | WO99/33504 | 7/1999 |
| WO | WO99/36009 | 7/1999 |
| WO | WO99.56802 | 11/1999 |
| WO | WO99/61815 | 12/1999 |
| WO | WO 00/02614 | 1/2000 |
| WO | WO 00/03757 | 1/2000 |
| WO | WO 00/44324 A1 | 8/2000 |
| WO | WO 01/04507 A1 | 1/2001 |
| WO | WO 01/30419 A2 | 5/2001 |
| WO | WO 01/68180 | 9/2001 |
| WO | WO 01/81785 A1 | 11/2001 |
| WO | WO 01/93926 A2 | 12/2001 |
| WO | WO 02/46080 | 6/2002 |
| WO | WO 02/066854 A1 | 8/2002 |
| WO | WO 02/094352 | 11/2002 |
| WO | WO 02/100457 | 12/2002 |
| WO | WO 02/068014 | 1/2003 |
| WO | WO 03/015860 A1 | 2/2003 |
| WO | WO 03/026728 | 4/2003 |
| WO | WO 2004/030726 A | 4/2004 |
| WO | WO 2004/087240 | 10/2004 |
| WO | WO 2005/004973 | 1/2005 |

\* cited by examiner

Fig. 3a
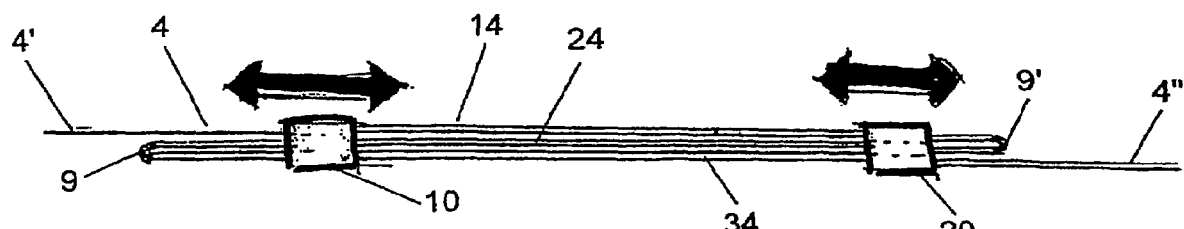
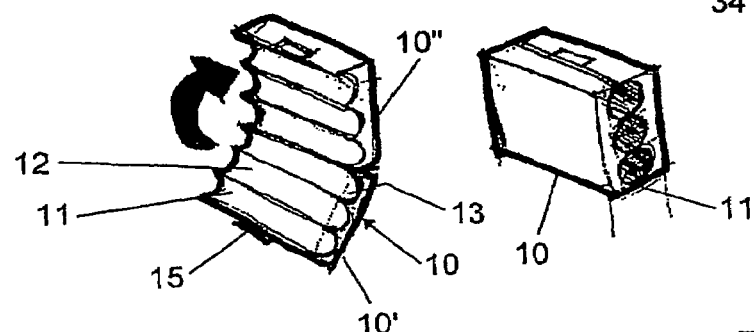
Fig. 3b
Fig. 3c

DEVICE FOR SUBCUTANEOUS ADMINISTRATION OF A MEDICAMENT TO A PATIENT

This application is a continuation of International Application No. PCT/DK2003/000569, filed Sep. 1, 2003, which is a continuation of Danish Application No. PA 2002 01284, filed Sep. 2, 2002, these references are incorporated herein in their entirety.

FIELD OF THE INVENTION

The present invention relates to a device for subcutaneous administration of a medicament to a patient, comprising a cannula housing with an interior chamber, a cannula connected to said cannula housing and being in flow communication with the interior chamber, and a flexible tubing having a first end and a second end, wherein the tubing is, at the first end, coupled to the cannula housing such that the tubing is in flow communication with the interior chamber, and wherein, at its second end, the tubing carries a source coupling by which the tubing can be coupled to a source for said medicament; and wherein, between its first and its second end, the tubing is folded for forming a controlled configuration of the tubing with essentially parallel courses of tubing.

BACKGROUND

U.S. Pat. No. 5,522,803, being now as a reference deemed to constitute a part of the present text, shows in FIGS. 1 and 2 a cannula housing to be adhered to the skin of the patient so as to enable continuous administration of a drug to the patient via a plastics needle introduced into the skin of the patient. At its one end a tubing features a coupling that is releasably secured to the cannula housing, whereby the tubing can be released from the cannula housing, eg when the patient is in the bath. At its other end the tubing features a source coupling by which the tubing can be coupled to a source, such as a pump, thereby enabling the drug to be fed to the cannula housing through the tubing.

In some situations, eg when the patient is asleep it is necessary to have a relatively long distance between the cannula housing and the source of the drug to enable the source of drug to sit on a table next to the patient. Thus there is a need for a comparatively long tubing, eg a tubing having a length of about 1.1 m. Conversely, a short tubing is typically desired when the patient is up and about, ie when the source of drug is carried by the patient, eg in a pocket in his clothes. To overcome this problem, it is an option to change tubing as day turns into night. This, however, may lead to waste of the usually very expensive medicament located in the long tubing.

It is previously been attempted to solve this problem by providing the source of drug with a winder mechanism for the tubing, see international patent application No. WO 96/35472. The winder mechanism described therein, however, cannot be manufactured at low costs and there is a risk of the winder mechanism getting stuck.

U.S. Pat. No. 4,406,042 discloses a tubing clips where variation of the distance between the ends of the tubing is by changing the size of a tubing loop that projects from the clips.

BRIEF SUMMARY OF THE INVENTION

It is the object of the present invention to provide a device for subcutaneous administration of a drug to a patient that can be manufactured at low costs and that enables variations in the distance between the source of drug and the cannula housing.

This is accomplished in that, the device comprises a first and a second holder and in order to secure the tubing in said configuration, it is received in guides in a first holder device arranged between the first and the second end of the tubing and in guides in a second holder device arranged at the first or second end of the tubing or between the first and the second end of the tubing with parallel courses running between the holder devices; and that the first holder device can be displaced along the tubing in a direction towards the second holder device by movement of the tubing along said guides in the first holder device. Hereby it is possible to vary the effective distance between the cannula housing and the source of drug between approximately the length of the tubing and a distance determined by the number of folds on the tubing and the position of the holder device; and to adequately control the courses of tubing and adequately support the tubing in the area around the folds. The second holder device may be an integral part of the cannula housing or the source coupling, or it may be configured in the same manner as the first holder device and may be arranged on the tubing as a separate component that is capable of being displaced along the tubing.

In the latter case, the effective distance between the cannula housing and the source of drug can be increased by manually displacing the holder devices towards each other along the tubing, ie along the respective courses of tubing, and then sort out the requisite length of tubing. Depending on the frictional resistance between the tubing and the holder device, said effective distance may alternatively be increased by merely applying a pull in the two ends of the tubing. The distance can subsequently be reduced by manually pulling the holder devices away from each other.

It is preferred that at least the first holder device is provided with guides for the tubing, preferably in the form of bores, ie closed channels, and these guides can be rectilinear or they can be curved and hence receive the fold(s) of the tubing and provide a certain protection of the tubing in these areas. Particular advantages from the point of view of mounting can be accomplished by configuring the one or both of the holder devices as a two-piece housing, thereby facilitating the mounting of the holder devices on the tubing.

In the present context, the term "parallel courses of tubing" is intended to designate one or two lengths of the tubing that has/have—apart from the folding area—courses that are mutually entirely parallel or converge towards each other within an angle interval of a very few degrees, eg 1-5°, so as to allow the courses of tubing to extend relatively close to each other irrespective of the position of the holder device along the tubing. Also, the term "folded" is intended to designate a state in which the tubing continues to be able to convey medicament from the one end of the tubing to the other.

The invention also relates to a medicament supply device as recited in claim 12 that is suitable for being mounted on an existing system for subcutaneous administration of a medicament.

BRIEF DESCRIPTION OF SEVERAL VIEWS OF THE DRAWINGS

The invention will now be explained in further detail with reference to the drawing.

FIGS. 3a, 3b and 3c show a variant of the embodiment of FIG. 2, wherein the cannula housing and source coupling are omitted.

DETAILED DESCRIPTION OF THE INVENTION

Figure 1:
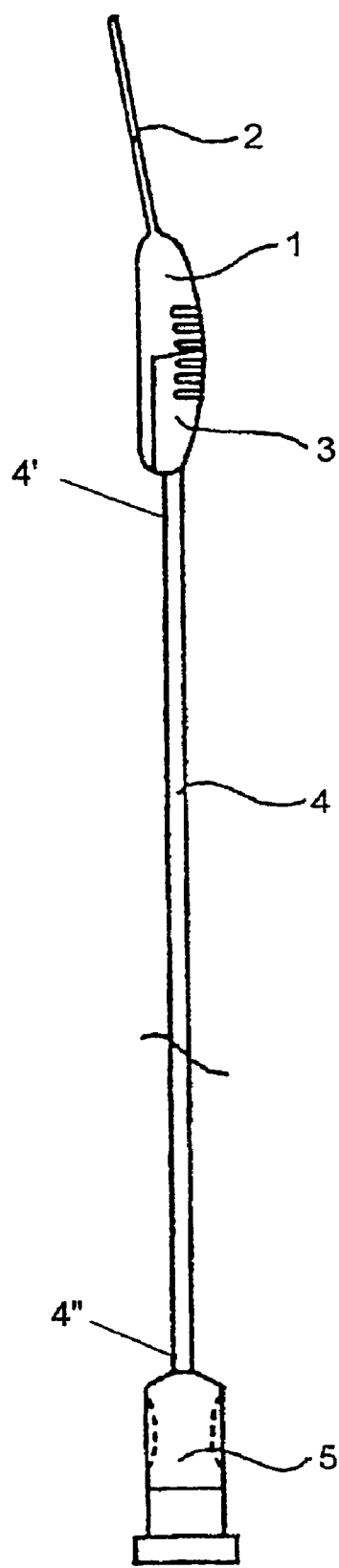
FIG. 1 is a schematic view of a number of the elements necessary for subcutaneous administration of a medicament to a patient.

FIG. 1 shows a part of a flexible tubing 4 having a first end 4' and a second end 4". At its first end 4' the tubing 4 is provided with a coupling 3 configured for being, in a releasable manner, able to be secured to a cannula housing 1. The cannula housing 1 has an interior chamber that communicates with the tubing 4 and with a cannula 2 that protrudes from the cannula housing 1 which is preferably flexible and of plastics and intended for being introduced through the surface of the skin of a patient by means of a not shown insertion needle. The interior chamber is not shown, but its configuration may like the one shown in U.S. Pat. No. 5,522,803.

A source coupling 5 secured to the second end 4" of the tubing 4 makes it possible to releasably couple the tubing to a source for a drug. The term 'source' in this context is intended to designate a receptacle for the drug, a pump preferably being introduced between the receptacle and, the coupling that, said pump supplying the drug to the patient via the tubing 4 in a predetermined dosage. The source coupling 5 is configured for being able to co-operate with a complementary coupling on said drug receptacle or on a tubing connected to the receptacle or pump. Preferably the tubing 4 is made of a plastics material and has such properties that, to a wide extent, the tubing 4 is able to prevent a local occlusion of the flow of the drug if the tubing 4 is folded sharply.

Figure 2:
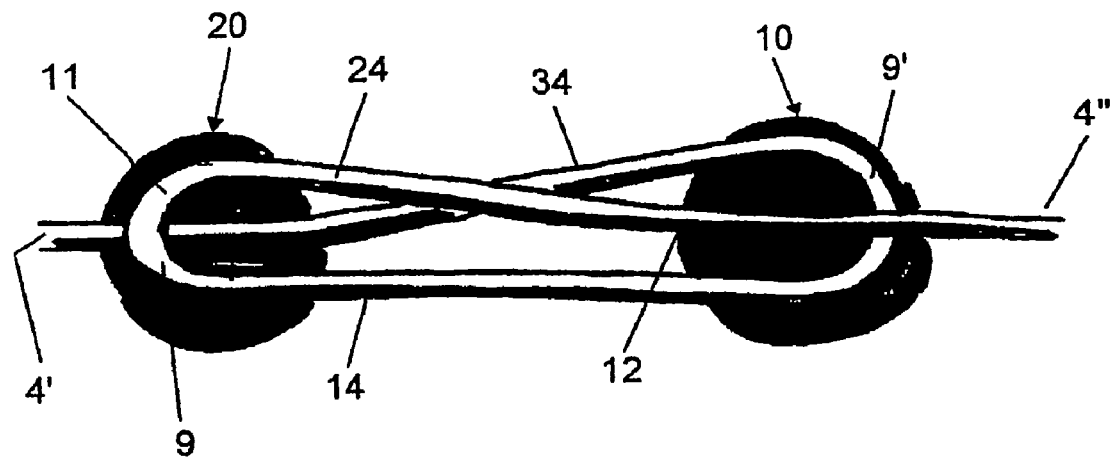
FIG. 2 schematically shows a sectional view of an alternative embodiment of the invention, wherein the cannula housing and source coupling are omitted.

FIG. 2 shows an embodiment of the invention, wherein two holder devices 10, 20 are used for providing a desire controlled configuration with three courses, 14, 24, 34 of tubing that extend between the holder devices 10, 20. Alternatively, it is certainly an option to configure the holder devices 10, 20 to form five courses of tubing.

The holder devices 10, 20 are shown in FIG. 2 in a schematic sectional view and each of the holder devices 10, 20 comprises an internal semicircular guide 11 and an internal rectilinear guide 12, respectively. The semi-circular guide 11 serves to receive the fold 9, 9' of the tubing, while the rectilinear guide 12 conveys the tubing 4 into the area between the two holder devices 10, 20. The width of the guides 11, 12 are adapted to the diameter of the tubing 4, such that the tubing 4 is able to slide in the guides 11, 12 with a desired minimum friction. In order to increase the distance between the cannula housing and the source coupling, a pull is merely exerted in the tubing 4 at its ends 4', 4", whereby the length of the individual courses of tubing is reduced, while simultaneously the holder devices 10, 20 move towards each other. Conversely, to increase the length of the courses 14, 24, 34 of tubings and thus to move the ends 4', 4" of the tubing 4 towards each other, a pull is merely exerted in the holder devices 10, 20 in a direction away from each other. In both situations the holder devices are displaced along the tubing 4, the tubing 4 sliding in the guides 11, 12.

FIG. 3a shows a variant of embodiment shown in FIG. 2, wherein the holder devices 10, 20 are split, the two parts 10', 10" being preferably articulated to each other and configured for being moved from an open state shown in FIG. 3b to a closed state shown in FIG. 3c, and to be secured in the latter state via a lock 15, such as a snap lock. Hereby the holder devices 10, 20 can be mounted in an existing system of the kind shown in FIG. 1. In this embodiment, the holder devices 10, 20 comprise three rectilinear guides 11, 12, 13 for the tubing 4.

Figure 4:
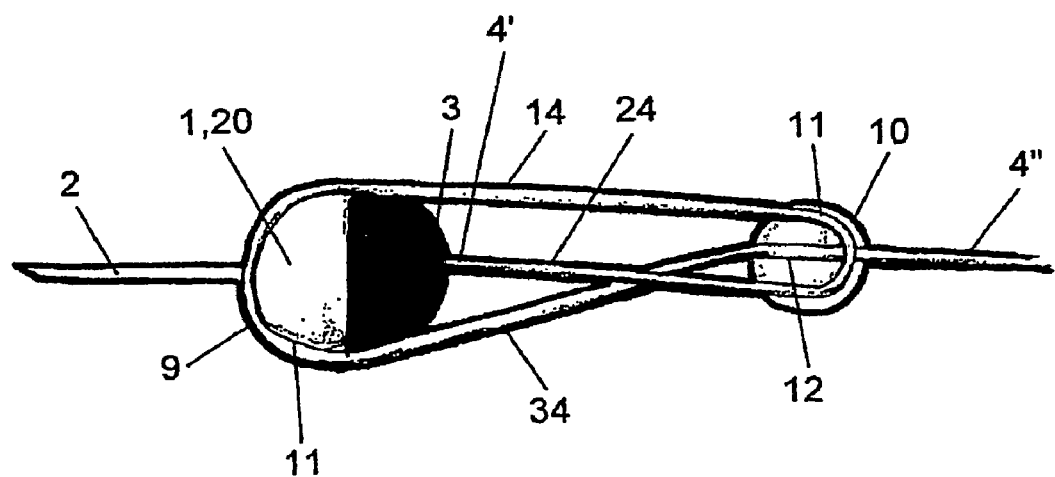
FIGS. 4, 5a and 5b are alternative embodiments, wherein the second holder device is configured as an integral part of the coupling to the cannula housing.

A further embodiment is shown in FIG. 4, wherein the first holder device 10 is configured as described above with reference to FIG. 2, but wherein the second holder device 20 is arranged at the first end 4' of the tubing 4 and is configured as an integral part of the cannula housing 1, said cannula housing 1 comprising an outer guide 11 for the fold 9 of the tubing 4. The guide 11 is preferably configured as a notch into which the tubing can be urged and that secures the tubing to the cannula housing 1. Like in the above-referenced embodiments, the guide 11 must be dimensioned such that the tubing 4 is able to slide in the notch when the first holder device 10 is pulled to the right in FIG. 4 to increase the length of the courses 14, 24, 34 of the tubings.

Figure 5A:
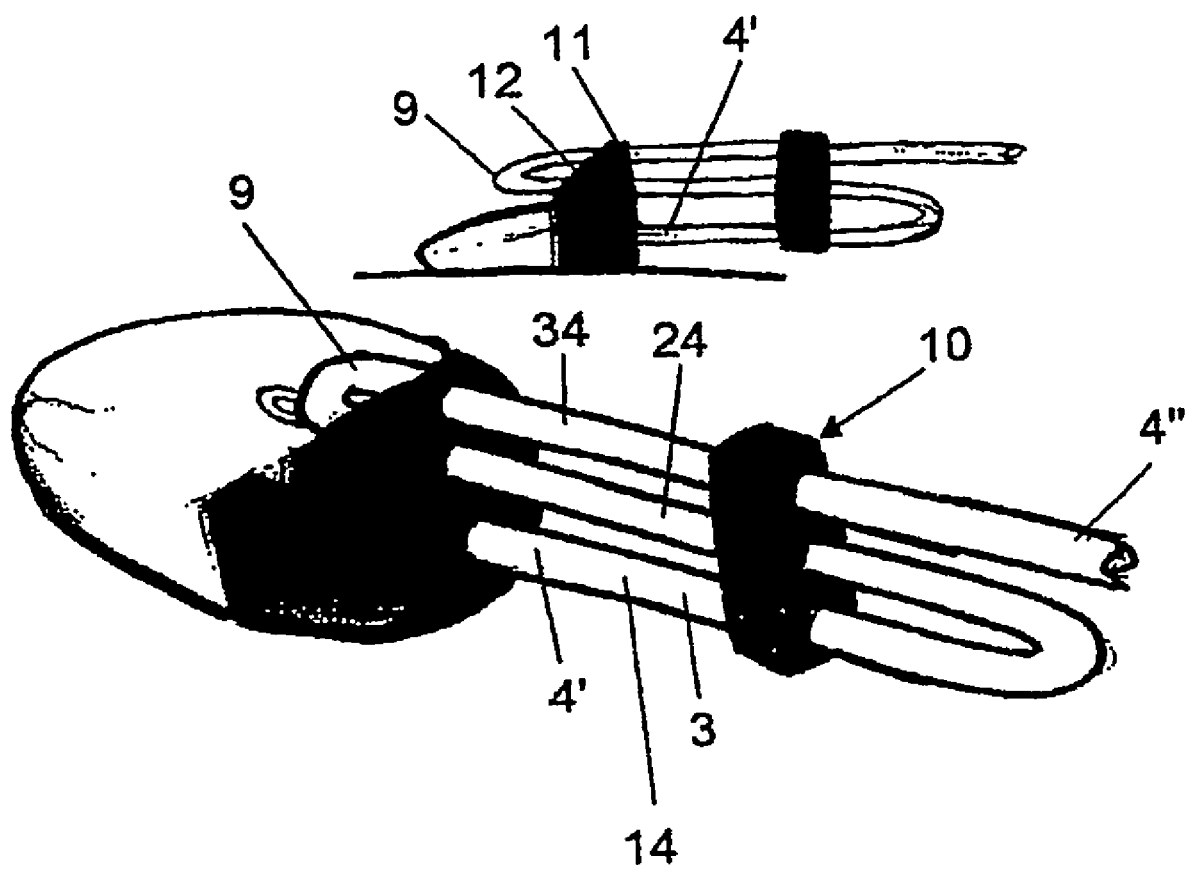
Figure 5B:
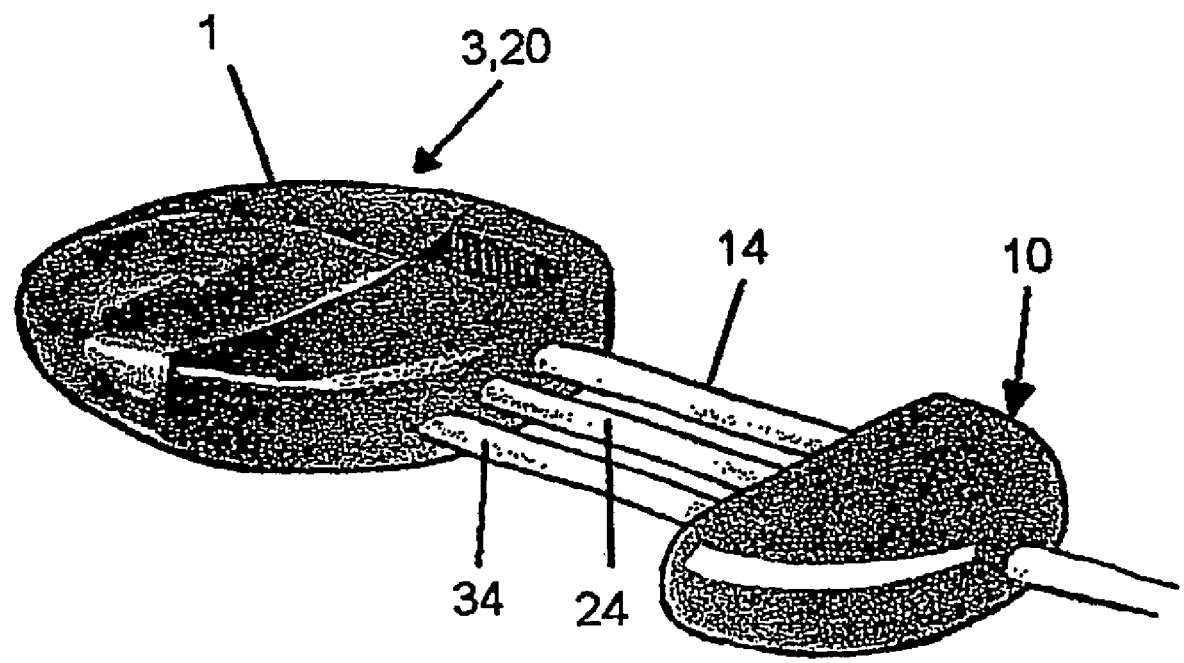

FIGS. 5a and 5b show alternative embodiments, wherein the second holder device 20 is arranged at the first end 4' of the tubing 4 and is configured as an integral part of the coupling 3, whereby the tubing 4 is connected to the cannula housing 1. Thus, the coupling 3 secures, firstly, the end 4' of the tubing and, secondly, it also comprises two guides in the form of bores 11, 12 that secure the tubing in the region at the fold 9. The first holder device 10 can be configured like the holder device 10 shown in FIG. 3c. An increase in the distance between the cannula housing 1 and the source coupling is accomplished merely by a pull in the tubing 4 at its ends 4', 4", whereby the length of the individual courses of tubing is reduced while simultaneously the first holder device 10 moves towards the second holder device 20. Conversely, an increase in the length of the courses 14, 24, 34 of the tubings, and hence movement of the ends 4', 4" of the tubing towards each other, is accomplished merely by a pull in the holder devices 10, 20 in a direction away from each other. In both situations the tubing 4 is displaced in the guides of the two holder devices 10, 20.

Figure 6:
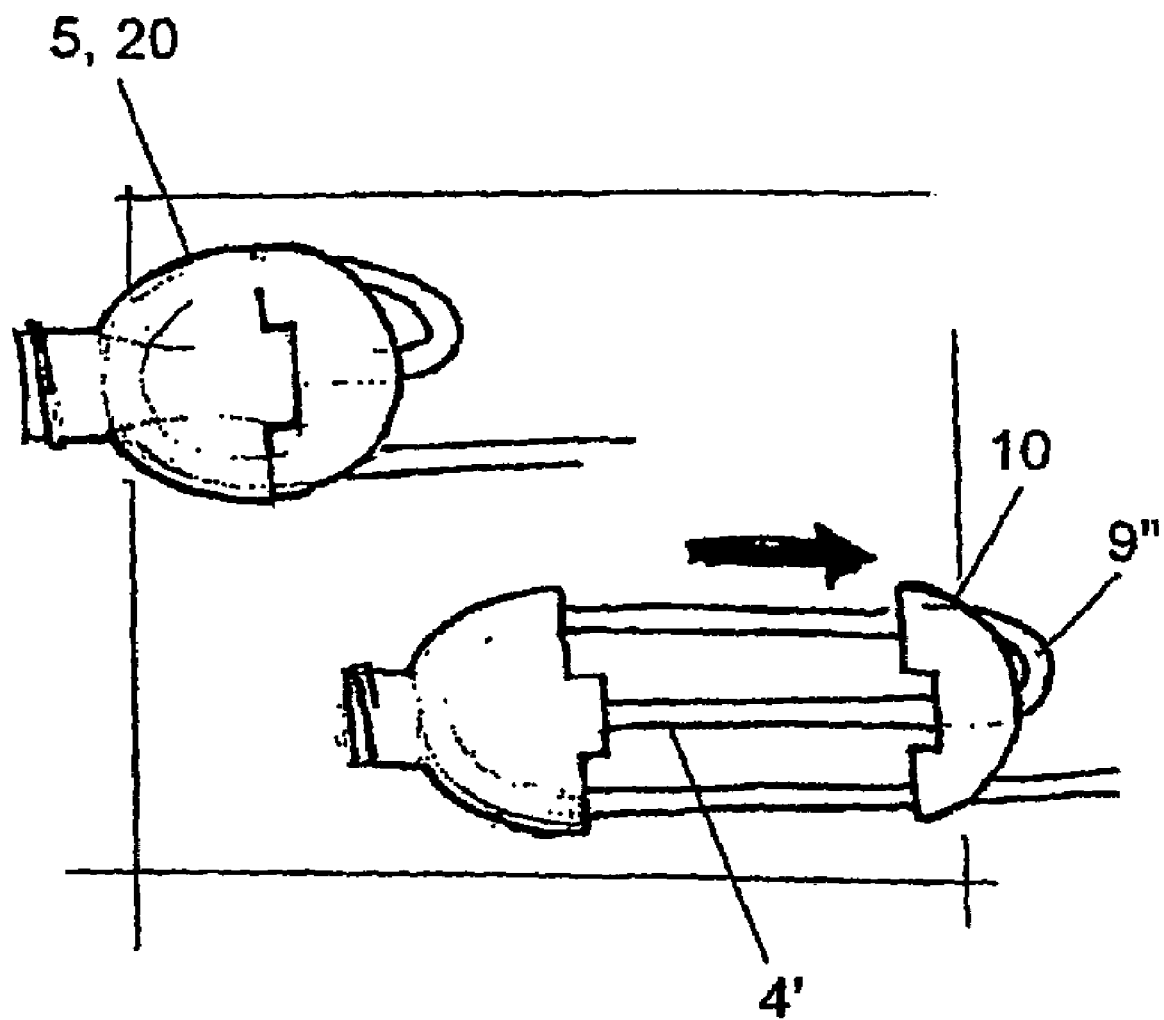
FIG. 6 shows an embodiment in which the second holder device is configured as an integral part of the source coupling.

Finally FIG. 6 shows an embodiment that, in principle, corresponds to the one shown in FIG. 5a, but wherein the second holder device is configured as an integral part of the source coupling 5. The first holder device 10 can optionally be configured such that it can be locked releasably to the second holder device 20 and be separated there from, when the distance between the courses of tubing is to be increased as is shown at the bottom of FIG. 6.

The invention claimed is:

1. A device for subcutaneous supply of a medicament to a patient, comprising:
   a cannula housing with an interior chamber;
   a cannula connected to the cannula housing and being in flow communication with the interior chamber;
   a flexible tubing having a first end and a second end, wherein the tubing is, at its first end coupled to the cannula housing, said tubing being in flow communication with the interior chamber; and wherein the tubing carries a source coupling, at its second end, by which the tubing can be coupled to a source for said medicament;

wherein the tubing is folded and forms a configuration with essentially parallel courses of said tubing;

wherein the device comprises a first and a second holder device said essentially parallel courses running between said first holder device and said second holder device, said holder devices each defining guides therein for securing the tubing to said holder devices, each holder device receiving at least two of said courses of tubing; and wherein the first holder device is freely slidable along the tubing towards the second holder device by movement of the tubing along said guides in the first holder device.

2. A device according to claim 1, wherein the first holder device is configured as a housing with at least two bores that form said guides.

3. A device according to claim 2, wherein the second holder device is arranged between the first and second ends of the tubing; and wherein the second holder device can be displaced along the tubing in a direction towards the first holder device.

4. A device according to claim 3, wherein the second holder device is configured as a housing with at least two bores that form said guides.

5. The device according to claim 3, wherein the second holder device comprises the source coupling.

6. A device according to claim 1, wherein the second holder device comprises the cannula housing or a coupling for connecting the tubing to the cannula housing.

7. A device according to claim 6, wherein the tubing is received in guides that extend interiorly of the cannula housing.

8. A device according to claim 1, wherein the second holder device comprises the source coupling.

9. A device according to claim 8, wherein the tubing is received in guides that extend interiorly of the source coupling.

10. A device according to claim 1, wherein the tubing is bent for forming at least three essentially parallel courses of tubing.

11. A device according to claim 1, wherein the first holder device and the second holder device comprises two housing parts configured for movement between a first position in which there is access to said guides for introduction into the guides of the tubing transversally to the longitudinal expanse of the guides, and a second position, in which the tubing is fixed against movement out of the guides transversally to the longitudinal expanse of the guides.

12. A device according to claim 1, wherein the guides are configured for being blocked, wherein removal of the tubing by withdrawal of the tubing transversally to the longitudinal direction of the tubing is prevented.

13. A device according to claim 1, wherein the first holder device or the second holder device comprises two housing parts configured for movement between a first position in which there is access to said guides for introduction into the guides of the tubing transversally to the longitudinal expanse of the guides, and a second position, in which the tubing is fixed against movement out of the guides transversally to the longitudinal expanse of the guides.

14. The device according to claim 1, wherein the tubing is slidably received in said first holder device.

15. The device according to claim 1, wherein said first holder device is releasably lockable to said second holder device.

16. A medicament supply device including a flexible tubing for supplying a medicament to a first end thereof with a cannula housing coupling for connecting said device to a cannula housing that has an interior chamber and a cannula connected to said cannula housing in flow communication with the interior chamber, from a second end thereof having a source coupling wherein the tubing can be coupled to a source of said medicament, wherein said tubing is, between the first and the second end folded, forming a configuration with essentially parallel courses of said tubing, wherein the device includes a first and, a second holder device, said essentially parallel courses running between said first holder device and said second holder device, said holder devices each defining guides therein for securing the tubing to said holder devices, each holder device receiving at least two of said courses of tubing; and wherein the first holder device is freely slidable along the tubing towards the second holder device by movement of the tubing along said guides in the first holder device.

17. A device according to claim 16, wherein the first holder device is configured as a housing with at least two bores that form said guides.

18. A device according to claim 17, wherein the second holder device is arranged between the first and second ends of the tubing; and wherein the second holder device can be displaced along the tubing in a direction towards the first holder device.

19. A device according to claim 18, wherein the second holder device is configured as a housing with at least two bores that form said guides.

20. A device according to claim 16, wherein the second holder device comprises the cannula housing coupling.

21. A device according to claim 20, wherein the tubing is received in guides that extend interiorly of the cannula housing coupling.

22. A device according to claim 16, wherein the second holder device comprises the source coupling.

23. A device according to claim 22, characterised in that the tubing is received in guides that extend interiorly of the source coupling.

24. A device according to claim 16, wherein the tubing is folded for forming at least three essentially parallel courses of tubing.

25. A device according to claim 16, wherein the first holder device and the second holder device-comprises two housing parts configured for being movable between a first position in which there is access to said guides for introduction into the guides-of the tubing-transversally to the longitudinal expanse of the guides; and a second position in which the tubing is fixed against movement out of the guides transversally to the longitudinal expanse of the guides.

26. A device according to claim 16, wherein the guides are configured for being blocked, wherein removal of the tubing by withdrawal of the tubing transversally to the longitudinal direction of the tubing is prevented.

27. A device according to claim 16, wherein the first holder device or the second holder device comprises two housing parts configured for movement between a first position in which there is access to said guides for introduction into the guides of the tubing transversally to the longitudinal expanse of the guides; and a second position in which the tubing is fixed against movement out of the guides transversally to the longitudinal expanse of the guides.

* * * * *